United States Patent
Jakob et al.

(10) Patent No.: US 10,683,240 B2
(45) Date of Patent: Jun. 16, 2020

(54) PRODUCTION METHOD FOR DIPEPTIDE-CONTAINING GRANULES

(71) Applicant: Evonik Operations GmbH, Essen (DE)

(72) Inventors: Harald Jakob, Hasselroth (DE); Hans Joachim Hasselbach, Gelnhausen (DE); Dominik Egly, Michelstadt (DE); Waldemar Hessberger, Alzenau (DE)

(73) Assignee: Evonik Operations GmbH, Essen (DE)

( * ) Notice: Subject to any disclaimer, the term of this patent is extended or adjusted under 35 U.S.C. 154(b) by 10 days.

(21) Appl. No.: 16/148,484

(22) Filed: Oct. 1, 2018

(65) Prior Publication Data

US 2019/0135708 A1    May 9, 2019

(30) Foreign Application Priority Data

Oct. 2, 2017 (EP) .................................. 17194295

(51) Int. Cl.
| | |
|---|---|
| *C05C 3/00* | (2006.01) |
| *C05F 11/10* | (2006.01) |
| *C05D 1/00* | (2006.01) |
| *C05G 5/12* | (2020.01) |
| *B01J 2/02* | (2006.01) |
| *C12P 13/12* | (2006.01) |
| *C05G 5/20* | (2020.01) |

(52) U.S. Cl.
CPC .................. *C05C 3/00* (2013.01); *B01J 2/02* (2013.01); *C05D 1/00* (2013.01); *C05F 11/10* (2013.01); *C05G 5/12* (2020.02); *C05G 5/20* (2020.02); *C12P 13/12* (2013.01)

(58) Field of Classification Search
None
See application file for complete search history.

(56) References Cited

U.S. PATENT DOCUMENTS

| | | | |
|---|---|---|---|
| 6,241,795 B1 * | 6/2001 | Svec | C05F 11/10 71/11 |
| 2003/0172698 A1 | 9/2003 | Koda et al. | |
| 2007/0131010 A1 * | 6/2007 | Binder | C05C 3/00 71/23 |
| 2016/0353773 A1 * | 12/2016 | Weissbrodt | A23P 10/20 |
| 2019/0322600 A1 * | 10/2019 | Koerfer | C05C 3/00 |

FOREIGN PATENT DOCUMENTS

| | | | | |
|---|---|---|---|---|
| CN | 104609945 | * | 5/2015 | C05G 3/00 |
| EP | 1 233 071 A2 | | 8/2002 | |
| EP | 1564208 | * | 8/2005 | C07C 319/20 |
| WO | WO 2018/001988 A1 | | 1/2018 | |

OTHER PUBLICATIONS

Extended European Search Report dated Mar. 13, 2018 in Patent Application No. 17194295.6.

* cited by examiner

*Primary Examiner* — Wayne A Langel

(74) *Attorney, Agent, or Firm* — Oblon, McClelland, Maier & Neustadt, L.L.P.

(57) ABSTRACT

The present invention relates to a process for producing a particulate composition containing methionine, methionyl-methionine, potassium in the form of potassium salt and ammonium sulfate, and use thereof.

13 Claims, 4 Drawing Sheets

Apparatus for carrying out a spray granulation

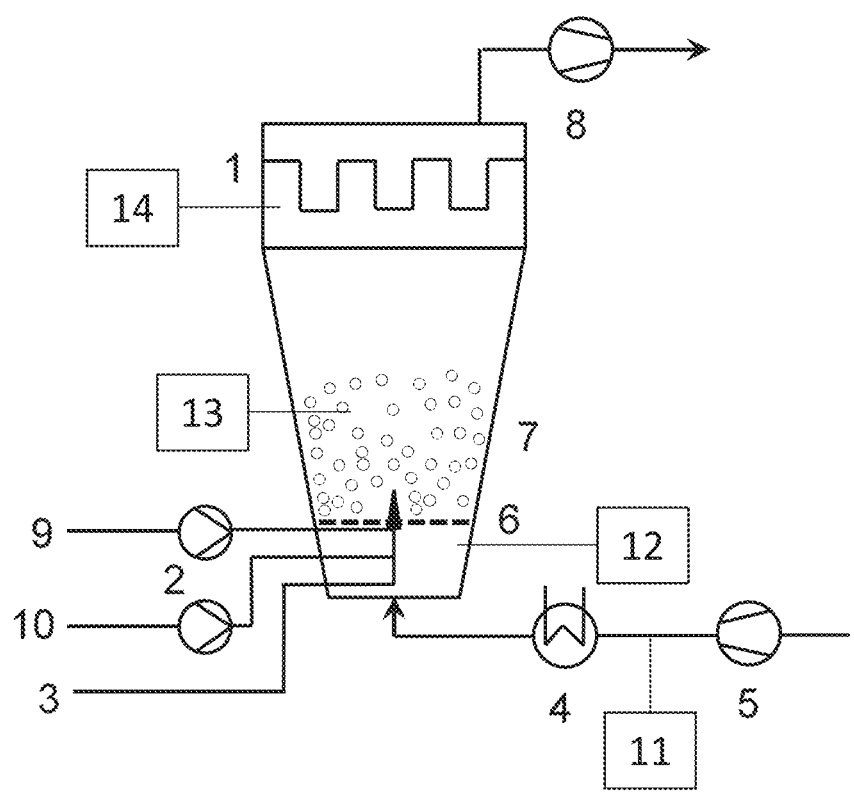
Figure 1: Apparatus for carrying out a spray granulation

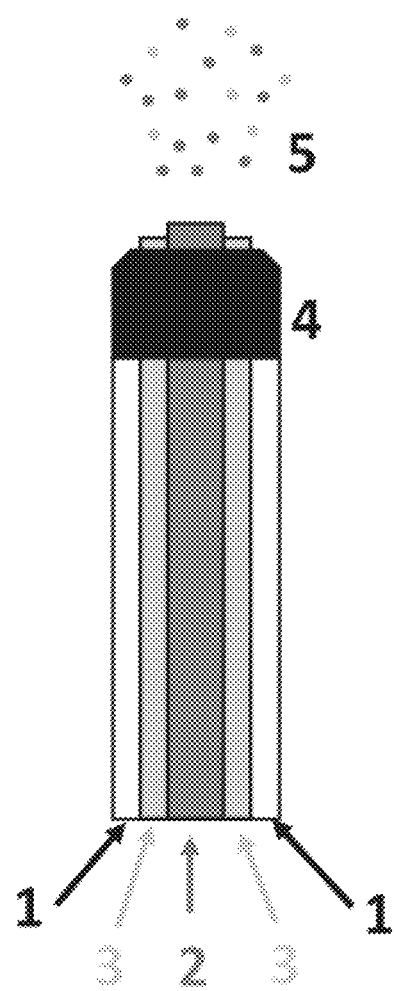
Figure 2: Three-fluid nozzle used

Figure 3: Distributor plate (glass frit) in the flow direction of the process gas. The three-fluid nozzle is centrally inserted in the bottom spray process in order to introduce the solutions/suspensions
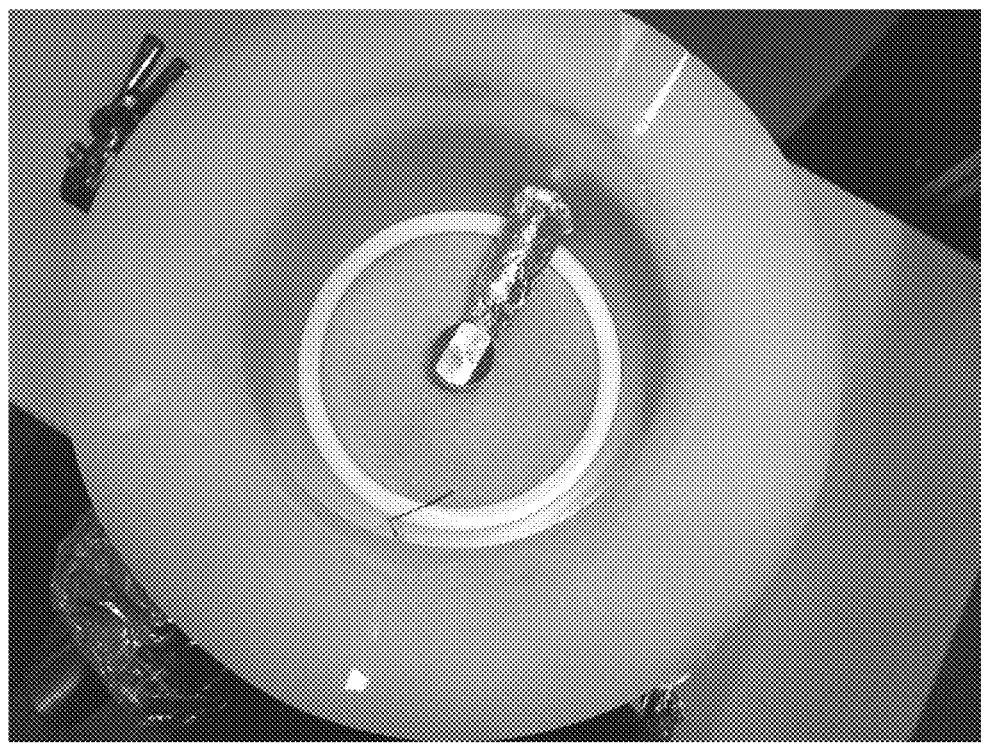

Figure 4: Storage stability and hygroscopicity:
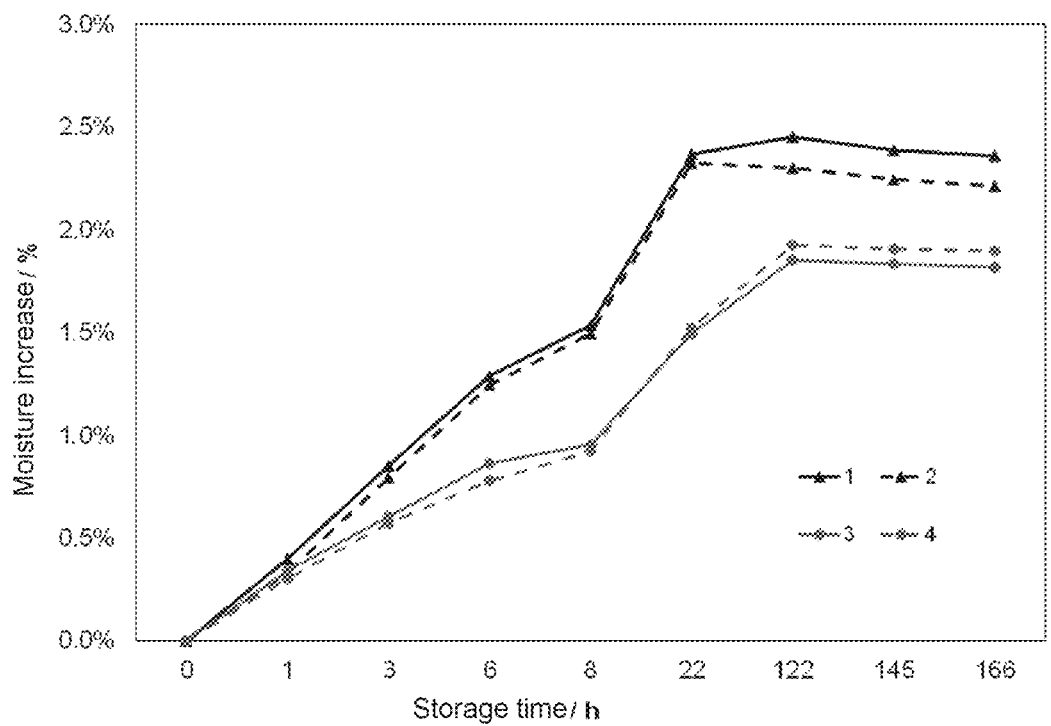

PRODUCTION METHOD FOR DIPEPTIDE-CONTAINING GRANULES

CROSS-REFERENCE TO RELATED APPLICATION

This application is based upon and claims the benefit of priority to European Application No. 17194295.6, which was filed on Oct. 2, 2017.

BACKGROUND OF THE INVENTION

The present invention relates in particular to a process for producing a particulate composition comprising methionine, methionylmethionine, potassium salt and ammonium sulfate, and to the use thereof.

The amino acid methionine is currently industrially produced worldwide in large amounts and is of considerable commercial importance. Methionine is employed in many fields, such as pharmaceutical, health and fitness products, but particularly as feedstuff additive in many feedstuffs for various livestock. On an industrial scale, methionine is produced chemically via the Bucherer-Bergs reaction, which is a variant of the Strecker synthesis. Here, the starting substances 3-methylmercaptopropanal (prepared from 2-propenal and methylmercaptan), hydrocyanic acid (hydrogen cyanide), ammonia and carbon dioxide are reacted to give 5-(2-methylmercaptoethyl)hydantoin (methionine hydantoin) and this is subsequently hydrolysed by alkali with potassium carbonate and potassium hydrogen carbonate to give potassium methioninate. Methionine is finally liberated from its potassium salt by treatment with carbon dioxide, which may be filtered off as a precipitate from the mother liquor containing potassium carbonate and potassium hydrogen carbonate (U.S. Pat. No. 5,770,769). The ammonia, potassium carbonate and potassium hydrogen carbonate reagents and also carbon dioxide are generally recycled in industrial methionine production. From time to time, however, it is necessary to replace some of the aqueous mother liquor in this hydantoin hydrolysis circulation with fresh potassium hydroxide, essentially in order to remove the potassium salt, deactivated in the form of neutral potassium formate, from the circuit ("purge"). Potassium formate forms from the residues of hydrogen cyanide and potassium salts from the hydantoin hydrolysis present in the methionine hydantoin solution (WO2013030068A2). A further by-product of methionine synthesis is the dipeptide methionylmethionine (EP 1 564 208 A1). In general, the excessive enrichment of by-products in the hydantoin hydrolysis circulation must be avoided since otherwise disruptions in the crystal formation occur downstream.

The so-called purge solution comprises approximately 2 to 6% by weight methionine, 4 to 8% by weight methionylmethionine and 6 to 14% by weight potassium in the form of potassium salts. Due to the potassium, nitrogen and sulfur content, this solution is suitable as a liquid fertilizer (C. C. Mitchel and A. E. Hiltbold, Journal of Plant Nutrition, 17(12), 2119-2134, 1994). It was desirable, however, to provide such a fertilizer in solid form. Attempts to dewater this solution to form a solid, free-flowing solids mixture, in order to make it easier to store and transport this valuable material, have nevertheless hitherto failed (cf. Example 6 in this document).

The object on which the present invention is fundamentally based, accordingly, was that of providing a solid fertilizer based on methionine and potassium salts, and also a simple and cost-effective process for its production, in which in particular the aqueous mother liquor of the above-described hydantoin hydrolysis circulation can also be used as a material of value.

BRIEF SUMMARY OF THE INVENTION

This fundamental object has been achieved by the finding of a process in which a gas, together with the aqueous starting mixture comprising methionine, methionylmethionine, potassium in the form of potassium salt, and ammonium sulfate, is sprayed as liquid component via a nozzle. This aqueous starting mixture was first of all generated from the aforementioned purge solution by controlled addition of ammonium sulfate solution. In the subsequent spray granulation of the aqueous starting mixture to form a free-flowing, storage-stable solid composition, a two-fluid nozzle was preferably used. This process is described in the hitherto unpublished EP publication with application number 16176371.9. The use of a two-fluid nozzle for the spray granulation, however, requires prior mixing of the starting solutions, namely the purge solution and the aqueous ammonium sulfate solution. If, additionally, the pH is adjusted into the acidic range by addition of $H_2SO_4$, then heat is generated and $CO_2$ is released, thus initiating a foaming of the mixture. Moreover, a sticky solid is precipitated, consisting very largely of Met-Met and methioninediketopiperazine. As a result of this sticky phase, the nozzles, pipelines and stirring containers become clogged over time. In order to prevent sticking of the nozzle and of the pipelines, the sticky phase can be broken down into fine droplets by means of a high-performance disperser prior to spraying, but this again implies additional cost and complexity.

The experiments described in the EP application with application number 16176371.9 also show that the fine droplets of the sticky phase become included in the end product because of the spray granulation technology. The production of the sticky phase, however, necessitates regular cleaning of the feed vessels, since wall deposits may build up over a prolonged period.

BRIEF DESCRIPTION OF THE DRAWINGS

FIG. 1 illustrates one embodiment of an apparatus for carrying out a spray granulation;

FIG. 2 illustrates one embodiment of a three-fluid nozzle;

FIG. 3 illustrates one embodiment of a distributor plate; and

FIG. 4 depicts a graph of moisture increase versus storage time.

DETAILED DESCRIPTION OF THE INVENTION

The specific object to be achieved, therefore, was that of finding a spray granulation process from which the disadvantages stated above are absent or are present only to a reduced extent. More particularly, in an extremely simple and direct way, it ought to be possible, from the purge solution and the aqueous ammonium sulfate solution, to produce a free-flowing, storage-stable solid composition of the type identified above.

The stated object is achieved by means of a process of spray granulation for producing a particulate composition comprising methionine, methionylmethionine, potassium salt and ammonium sulfate, characterized in that (a) a first aqueous solution or suspension (i), comprising 30 to 40% by weight ammonium sulfate,
a second aqueous solution or suspension (ii), comprising
2 to 6% by weight, preferably 3 to 5% by weight methionine,
4 to 8% by weight, preferably 5 to 7% by weight methionylmethionine and
6 to 14% by weight, preferably 8 to 12% by weight potassium in the form of potassium salt and
a gas are sprayed into a fluidized bed via a three-fluid nozzle to produce crude particles,
with simultaneous evaporation of water, and optionally
(b) the crude particles obtained in step (a) are dried.

The two aqueous solutions or suspensions (i) and (ii) may comprise more or less undissolved constituents depending on the concentration used.

The second aqueous solution or suspension (ii) may also include significant amounts of sodium in the form of sodium salt, generally up to 4% by weight, preferably up to 3% by weight, sodium. This is especially the case when beforehand mixtures of potassium hydroxide and sodium hydroxide, potassium carbonate and sodium carbonate and/or potassium hydrogencarbonate and sodium hydrogencarbonate have been used as saponifying agents in the alkaline hydrolysis reaction of methioninehydantoin to alkali metal methioninate, as described for example in the EP patent application with EP application number 17171060.1.

The process is in any case simple and cost-effective to carry out in common apparatuses.

By means of the three-fluid nozzle, the starting media, purge solution (second aqueous solution or suspension ii) and ammonium sulfate solution (first aqueous solution or suspension i), respectively, advantageously do not have to be premixed in a mixing vessel prior to spraying; instead, mixing takes place shortly after the nozzle. FIG. 2 illustrates the principle of a three-fluid nozzle. The nozzle possesses two inlets (ports) for the liquid starting media and one inlet for the gas (e.g. nozzle air). The solutions for spraying are supplied to the nozzle device by means, for example, of a suitable pump. The two channels for the flow of the solutions to the nozzle are sited on the one hand as a central pipe, optionally with extension, and on the other hand as an inner annular gap between the central pipe and an inner jacket pipe enveloping this central pipe. The channel for the gas is formed in turn by an outer annular gap between the inner jacket pipe and an outer jacket pipe enveloping the inner jacket pipe, as shown in FIG. 1 of EP 716640 B1, for example. The outlets of all three channels open into the nozzle head. It is possible in principle to use other embodiments of three-fluid nozzles as well, corresponding to the fundamental functionality shown here. It is also possible to use four-fluid nozzles which are operated as a three-fluid nozzle. When a four-fluid nozzle is used, another possible procedure is to use the fourth inlet to supply the sulfuric acid for acidifying the ammonium sulfate solution or suspension (i). This has the advantage that the step of acidifying the ammonium sulfate solution need not be done beforehand and instead takes place directly in situ during the spray granulation.

Via the port to the central pipe, the first aqueous solution or suspension (i) (ammonium sulfate solution, optionally admixed with additional $H_2SO_4$) is fed in, and the addition of the second aqueous solution or suspension (ii) (e.g. purge solution) takes place via the second port to the inner annular gap. The two channels for supplying the two aqueous solutions or suspensions (i and ii) may also be switched with one another. The gas, in contrast, is introduced via the third port into the outer annular gap, the channel suitable for this purpose, and has the function of atomizing the liquid media into fine droplets, in order to distribute them within the process space and spray them, for example, into the fluidized bed (fluidized solid) present therein. The gas, preferably hot air or nitrogen, is at the same time caused to stream from bottom to top in the apparatus, in order firstly to fluidize the material present and secondly to evaporate the sprayed liquid (FIG. 1).

The solid sprayed ideally remains adhered to the particles present whereby a discrete particle growth can be adjusted. The particle size to be achieved in the discharge is dependent on the nucleus balance in the fluidized bed system. This is determined essentially by the equilibrium of nucleation by abrasion or non-impinging spraying droplets, and the construction of granules. The particle size can be adjusted in a controlled manner by selecting the drying and spraying parameters and by the use of a chopper in the fluidized bed. The granules thus produced can be discharged continuously from the drying chamber in target particle size by means of classifying facilities (e.g. sifter and underflow weir).

A preferred procedure here is one wherein the aqueous solution or suspension (ii) is used in a weight ratio to the aqueous solution or suspension (i) of 1.0/0.5 to 1.0/3.0, since on the one hand the desired particle composition is readily achievable by this means, and on the other hand the spray granulation can be operated advantageously.

With further preference, air or nitrogen is used as gas, since both are available on favourable terms and the resulting offgas can be supplied without problems to a combustion facility.

The spray granulation process a) is carried out preferably in a fluidized bed, more particularly at a temperature in the fluidized bed of 60 to 130° C., since on the one hand the desired particle properties are readily achievable by this means and on the other hand the spray granulation can be operated advantageously.

Further advantages of the spray granulation process carried out using a three-fluid nozzle are as follows:
There is no need for a mixing vessel and cooling of the vessel for the prior mixing and pH adjustment of the starting media.
Foam formation and development of the sticky phase are avoided.
The heat given off by the pH adjustment with $H_2SO_4$ can be utilized for the granulating process.
Improvement is achieved in product properties such as hygroscopicity and storage stability.
In contrast to the granules obtained with a two-fluid nozzle (described in EP 16176371.9), the granules produced in accordance with the invention have significantly reduced caking tendency and lower hygroscopicity.

As a second aqueous solution or suspension (ii), it is possible advantageously directly to use the aqueous mother liquor obtainable by isolation from the aforementioned process for producing methionine, with the process comprising at least the steps of hydrolysing 5-(2-methylmercaptoethyl)hydantoin with potassium carbonate, potassium hydrogencarbonate to give aqueous potassium methioninate (hydantoin hydrolysis circulation in industrial production of methionine),
neutralizing aqueous potassium methioninate with carbon dioxide to form methionine and subsequently crystallizing the methionine.

The mother liquor containing material of value is passed on in an environmental way for proper recovery.

The first aqueous solution or suspension (i), which contains ammonium sulfate, can advantageously originate directly from the production of hydrogen cyanide from methane and ammonia that is necessary for the large-scale industrial production of methionine, as for instance hydrogen cyanide production by the Andrussow process (U.S. Pat. No. 8,802,020 B2) or the BMA process (F. Endter, Chemie-Ing-Techn. 30, 1958, No. 5, 305-310), and is formed substantially by treatment of a gas mixture produced in each of these processes, and containing hydrogen cyanide and ammonia, with aqueous sulfuric acid (sulfuric acid scrub) and subsequent neutralization of the resultant aqueous solution with ammonia. This solution is thereby supplied simultaneously in an environmentally friendly manner as a useful recovery.

In this manner, two additional streams of materials of value obtained from industrial methionine production are immediately transferred to a novel advantageous product without the necessity of further additives.

The potassium salt can take the form of either one salt or two or more salts of inorganic or of organic acids, for example at least one potassium salt selected from the group comprising formic acid, acetic acid, propanoic acid, 2-hydroxypropanoic acid, 2-hydroxy-4-methylthiobutanoic acid and also methionine and methionylmethionine at appropriate pH, potassium hydrogen carbonate, potassium carbonate, potassium hydrogen sulfate and potassium sulfate. Where, as a result of the process, there are significant amounts of sodium in the form of sodium salt, the sodium salts in question are more particularly those corresponding to the potassium salts stated here.

The first aqueous solution or suspension (i). e.g. ammonium sulfate solution, is admixed preferably before its further processing in step (a) with just the quantity of sulfuric acid so as to give, after the spray granulation, a particulate composition which on dissolution in water has a pH of 3 to 6, preferably of 3.5 to 5.5, measured at room temperature on a 10% by weight solution of the particulate composition in water by means of a glass pH electrode with liquid electrolyte (3-molar KCl solution) filling. The precise amount of sulfuric acid to be added is dependent in particular on the existing pH of the aqueous solutions or suspensions (i) and (ii) used, and may be easily determined in each case in preliminary experiments.

In the case of the processing of the solutions or suspensions (i) and (ii) in step (a), there is in part formation, from ammonium sulfate and potassium carbonate, of ammonium carbonate, which on heating decomposes to form ammonia and carbon dioxide and escapes in the form of these gases. By addition of sulfuric acid to the solution or suspension (i), the release of ammonia is very largely prevented, and it is bound again in the form of ammonium sulfate, with essentially only carbon dioxide escaping. A further effect of the setting of the pH at 3 to 6 is to improve the storage stability of the particles obtained in step (b) of the process according to the invention. The deposition of a sticky phase is additionally and advantageously prevented by this means.

In the case of one advantageous embodiment of the process according to the invention, the first aqueous solution or suspension (i) used in step (a) is concentrated before step (a) by evaporation of the water to give an aqueous suspension having up to 70% by weight solids content. This concentrate generally forms a stable suspension. The concentration process saves on energy costs in the process.

The process according to the invention may be carried out both as a batchwise process and as a continuous process, as for example in a fluidized bed or moving bed granulator or a mixing granulator.

The spray granulation here is carried out preferably in a fluidized bed, alternatively by the bottom spray or top spray process. Such a process enables the formation of particularly uniform particles of the particulate composition according to the invention with a relatively narrow particle size distribution. The particle size to be achieved in the discharge is in this case dependent on the nucleus balance in the fluidized bed system. This is determined essentially by the equilibrium of nucleation by abrasion or non-impinging spraying droplets, and the construction of granules. The particle size can be adjusted in a controlled manner by selecting the drying and spraying parameters and also by the use of a chopper. The granules thus generated can be discharged continuously from the drying chamber in the desired particle size by a classifying unit (e.g. sifter, underflow weir). The particle size of the product can be adjusted more narrowly by means of a downstream sieve. The oversized particles from the sieving are comminuted by a mill and are recycled together with the fine particles separated by cyclone (e.g. pneumatically or by conveying screw). This has the purpose that sufficient nuclei for the granulation are present in the process chamber and no product is lost.

The spray granulation is carried out at a temperature in the fluidized bed of 60 to 130° C., preferably 80 to 110° C. The operating pressure has little influence on the process. The process is typically operated at a slightly reduced pressure of 5 to 50 mbar, preferably of around 10 mbar, in order to avoid the discharge of dust from the system.

The spray granulation is also preferably carried out via one or more nozzles with 1.0 to 8.0 mm nozzle diameter, at nozzle pressures of 1.0 to 5.0 bar, ideally 2.0 to 3.0 bar. The spray rates of the mixture used should be chosen as a function of the system size.

The nozzle type used is a three-fluid nozzle (pneumatic atomizer), preferably with a circular solid cone as atomizer form (e.g. from Schlick).

To the particles obtained in step (a) or (b) of the process according to the invention it is additionally possible, by spraying with an aqueous solution containing 30 to 40% by weight ammonium sulfate, with simultaneous evaporation of the water, to apply an ammonium sulfate shell layer, with the proportion of the ammonium sulfate shell layer thus formed on the particles being 5 to 30% by weight, based on the total weight of the particles formed. The particular advantage in this case is that the shell layer additionally encloses unpleasant odour components and in this manner an almost odour-neutral product is generated. The spraying of the particles may usefully take place directly in the apparatus used for the spray granulation, by means of the three-fluid nozzle which is present. It is likewise possible, however, to carry out the spraying via a two-fluid nozzle. The aqueous ammonium sulfate solution to be used for the spraying may be identical to the aforementioned first aqueous solution or suspension (i), i.e., for example, it may also originate from the production of hydrogen cyanide.

On a smaller scale, the batchwise mode is preferred, i.e. the coating takes place after the granulation process. On an industrial production scale, the continuous mode is preferred. The granulator is preferably subdivided for this purpose into several zones. The first zones are used for the granulating step (a). Then a coating zone, a subsequent drying zone and a cooling zone follow for the appropriate processing of the granules primarily formed. The subsequent drying and cooling may also be carried out in separate systems (e.g. fluidized bed dryer/cooler with integrated heating and cooling elements). Suitable granulators are typical fluidized bed or moving-bed systems.

The particulate composition produced by the process according to the invention is suitable for use as a fertilizer or fertilizer additive, more particularly as a nitrogen/potassium/sulfur (NPS) fertilizer for application to areas of cultivation for crop plants. Compared to the purge solution used to date as liquid fertilizer, said composition has a distinctly higher active ingredient concentration and also better storage properties and product stability. The product is also non-hazardous from a safety perspective. For example, it is not a combustible dust product. The necessity for liquid transport and storage in appropriate tanks or tanker vehicles is also dispensed with. The product may also be delivered to customers in smaller containers. e.g. sacks or big bags.

The particulate composition produced according to the invention has an average particle size of around 1 to 4 mm. This has the advantage, especially in relation to larger particles, that it can be distributed relatively uniformly on the cultivation areas and therefore that an overdosing or underdosing in the context of application as a solid fertilizer can more easily be avoided.

The particulate composition produced according to the invention by spray granulation using a three-fluid nozzle has a lower moisture absorption on storage under hot and moist conditions as compared with a particulate composition produced by means of a two-fluid nozzle (Example 2), and on the same basis also has a significantly reduced caking tendency (Example 3), resulting in more favourable handling and processing properties, such as improved flow properties, for example.

Since the ammonium sulfate present in the composition according to the invention itself reduces the caking of the particles, the addition of a binder and/or flow aid is generally superfluous. Nevertheless, if a binder or flow aid is intended to be used for the production of the fertilizer compositions according to the invention, this is introduced advantageously, in the case of a batchwise mode of operation of a fluidized bed granulator, by mixing the binder or flow aid with the starting material in the fluidized bed. Suitable starting material (carrying material) is, in particular, the residue of the evaporated and dried second aqueous solution or suspension (ii) and/or the mother liquor (purge solution) from the hydantoin hydrolysis circulation described at the outset, which has been comminuted beforehand, for example, with a screen mill to a suitable average particle size of e.g. d50=150 μm. As an alternative, methionine powder (e.g. having a particle size d50=180 μm) or Ekoperl—an oil binder composed of porous volcanic silicate rock (perlite) e.g. in the grain size 0.125 to 2 mm—may also be used as starting material.

Suitable as binder are, for example, porous volcanic silicate rock (e.g. perlite), precipitated or fumed silica or porous carbonate rock.

In the case of the continuous mode of operation, e.g. a production process, the binder or flow aid is advantageously added by means of injector, suction cycle conveying, pneumatic conveying, rotary valve, stirred feed vessel or conveying screw.

EXAMPLES

Example 1

The spray granulation trials with a three-fluid nozzle were carried out in batch mode on a laboratory fluidized bed granulating unit (Glatt ProCell AGT150; see diagrammatic construction in FIG. 2). The experiments confirm unproblematic production of stable granules without instances of caking and encrustation of the fluidized bed chamber and of the three-fluid nozzle (see FIG. 3). The trials also show that the short mixing times are sufficient to bind the ammonia and to prevent the development of a sticky phase.

Suitable Apparatus and General Description of the Performance of the Process

The fluidized bed granulating unit used, from Glatt (ProCell), is shown diagrammatically in FIG. 1. The cylindrical process chamber is 300 mm high and possesses a diameter of 150 mm. Dust was collected from the process air by internal textile filters (6 filter bags). These filters were cleaned in countercurrent to the process air by a pulse of compressed air. Alternatively to a filter separator it is also possible, for example, to use a cyclone. The process gas was fed from the central nitrogen network and was conveyed through the unit by a fan operating in suction mode. The pressure prevailing in the process chamber was therefore reduced pressure (around −10 mbar). Before entering the process chamber, the air was heated directly by an electric heater (9 kW, from Helios). The heated air subsequently flows through a glass frit, which acts as a distributor plate to the particles. The narrow pore distribution provides for uniform distribution of the flow. In the upwardly directed gas stream, the particles were placed into a fluidized state in the process chamber, and the sprayed liquid was evaporated as a result of the introduction of heat by the drying air. The sprayed solid here remains, ideally, adhering to the particles present, thereby allowing the establishment of a discrete particle growth. The particle size to be achieved in the discharge is dependent on the nucleus balance in the fluidized bed system. This is determined essentially by the equilibrium of nucleation by abrasion or non-impinging spray droplets, and the construction of granules. The particle size can be adjusted in a controlled manner by selecting the drying and spraying parameters and by the use of a chopper in the fluidized bed. The granules produced in this way can be discharged continuously in target particle size from the drying chamber through a classifying facility (e.g. sifter, overflow weir).

In the example, granulation was carried out in a batch process without continuous discharge of product.

Set centrally into the glass frit is a three-fluid nozzle via which it is possible to introduce the aqueous solutions/suspensions (solution or suspension (i) or (ii), respectively, optionally in concentrated form) into the fluidized bed for granulation of the particles. For simplification, the description also uses the term "solution i" or "solution ii" for the term "solution or suspension (i)" and "solution or suspension (ii)", respectively.

Spray introduction took place by means of a bottom spray process. In this system, process gas and spray jet from the nozzle entered the process chamber cocurrently from below. The three-fluid nozzle used is an in-house construction by Evonik Industries AG, consisting of original parts from Schlick (swirl element, spindle and air cap, type 946 S1, from Düsen-Schlick GmbH). The three-fluid nozzle has an extended middle pipe; the central pipe is around 1 mm shorter than in the state as supplied from Düsen-Schlick. The air cap of the nozzle is not depicted in FIG. 2. FIG. 3 shows the position of the nozzle in the distributor plate.

For spray granulation in the above-described apparatus in accordance with Example 1, the aqueous solutions, in the composition given below, were used in a solution (ii): solution (i) mixing ratio of 1:2.

Aqueous solution (i): 35% by weight ammonium sulfate
Aqueous solution (ii) 4.6% by weight methionine 6.3% by weight methionylmethionine
9.7% by weight potassium Solution i and solution ii were each withdrawn from a plastic canister at room temperature. To avoid release of NH$_3$, 20% strength sulfuric acid was added to the first aqueous solution or suspension (i). This solution i+H$_2$SO$_4$ was homogenized in a mixing vessel and a magnetic stirrer prior to spraying. The two feed vessels with the solution i and, respectively, i+H$_2$SO$_4$ and solution ii were placed on a balance (measuring range up to 6 kg) in order for nozzle introduction (spraying rate) to be determined gravimetrically by the decrease in weight of the feed vessel. The solutions/suspension were withdrawn from the feed vessels and introduced into the process chamber, using the following pumps:

|  | Solution ii (purge solution) | Solution i (ammonium sulfate solution) + H$_2$SO$_4$ |
|---|---|---|
| Pump | Watson & Marlow peristaltic pump 503 U | Watson & Marlow peristaltic pump 505 U Head for assembled tubes |
| Tube | Silicone, Øi 4.8 * 1.6 (Verder tube) | Øi 2.79 purple-white Marprene |

The process parameters established for the process are listed in Table 1 and were detected continuously during the trial with the designated probes/sensors.

TABLE 1

Process parameters and their determination.

| Process parameter | Display value | Probe/sensor |
|---|---|---|
| Gas entry temperature | °C. | Thermocouple 2FK(J)AC10(iron-constantan), diameter 1 mm |
| Gas volume flow rate | m$^3$/h | Impeller flow sensor FA (cylinder probe), model ZS25GA-mn40/140/p6 170 mm, from Höntzsch |
| Fluidized bed temperature | °C. | Resistance thermometer PT 100, class A, 4 leads |
| Mass flow rate of the solutions jetted in* | kg/h | Weight decrease of the feed vessels (gravimetric); solution ii by Sartorius Universal U6100 balance/measuring range up to 6 kg; solution i + H$_2$SO$_4$ by Sartorius model F 150 S-DJZ/measuring range up to 150 kg; |

*= separate measurement, not integrated into the process control system of the fluidized bed unit Preparation of the Materials The second aqueous solution or suspension (ii) was sprayed directly without prior processing. Concentration of ii by evaporation beforehand is always possible and is advisable in a large-scale industrial process for reasons of energy.

Provision of solution i+H$_2$SO$_4$ by addition of sulfuric acid to the first aqueous solution or to suspension (i)
1. Solution i was introduced initially,
2. Addition of 20% strength sulfuric acid to a concentration of 4.4% by weight H$_2$SO$_4$ in the final mixture (corresponding to solution i+H$_2$SO$_4$)

The two solutions were sprayed separately from one another into the process chamber and the existing starting material, using the three-fluid nozzle. Serving as the starting material was a mixture of the dried solution i and ii. Before being used, the dried starting material was comminuted to a particle size of 600 μm by means of a screen granulator FGS from Erweka, Heusenstamm. Then 500 g were weighed out and used as the starting charge. As an alternative, methionine powder (particle size d50=180 μm) or Ekoperl—an oil binder composed of porous volcanic silicate rock (perlite) with grain size e.g. 0.125 to 2 mm—can also be used as starting material.

Preparation of the Apparatus

The starting material in the fluidized bed granulator was heated to a product temperature of 80-90° C., with a gas entry temperature of 120° C. Solutions ii and i+H$_2$SO$_4$ were subsequently conveyed via peristaltic pumps to the nozzle, from where they were sprayed into the fluidized bed onto the starting material.

Fluidization took place with an air volume flow rate between 40-200 m$^3$/h. This corresponds to a flow rate of 0.6-3.1 m/s in the case of the prevailing area of flow impingement (0.018 m$^2$). At the entry to the unit, the gas volume flow rate was measured using an impeller wheel (see FIG. 1). The entering air here was initially cold and dry. It subsequently passed through an electric heater. Located below the distributor plate in the unit was a temperature sensor which determines the gas temperature immediately below the distributor plate and hence prior to the entry of the gas into the process chamber (FIG. 1, temperature measurement point 1). This gas temperature is used as a control variable and was predetermined. The input of energy via the gas heater was controlled in harmonization with this measurement value, and the process air was heated to the temperature predetermined at the distributor plate.

Depending on the heating energy introduced, there is a change in the temperature of the air at the distributor plate. Consequently, the gas volume flow rate through the unit was adapted accordingly, so as to have a constant volume flow rate, taking account of the gas density at the distributor plate. This took place automatically by means of the process control system of the fluidized bed unit, said system controlling the fan mounted on the suction side.

Example 1 was carried out discontinuously in the above-described apparatus in accordance with FIG. 1. The experimental parameters set here were as follows:

Parameters Set in the Fluidized Bed Spray Granulation:
T air supply=100-200° C.
T fluidized bed=60-110° C.
T exhaust air=60-130° C.
Spraying rates=1 kg/h of solution ii and 2.6 kg/h of solution i+H$_2$SO$_4$
Nozzle pressure (three-fluid nozzle)=1.2 bar
Drying air volume flow=40-200 m$^3$/h. This corresponds to a flow velocity of 0.6-3.1 m/s at the stated inflow area (0.018 m$^2$)
System pressure above the sieve tray=10 mbar below atmospheric pressure
Mean residence time: 0.5-3 h.
Evaluation and Results: Product Properties:

TABLE 2

Product properties of the resultant spray granules

| No. | BD [kg/l] | Diameter (mm) | Tendency to dust formation | Flowability | Caking tendency | Composition (K:N:S) | Odour | pH |
|---|---|---|---|---|---|---|---|---|
| 1 | 0.75 | 1-2 | slight | good | slight | 11:14:19 | slight | 4.1 |

The pH of the particulate composition was measured on a 10% solution of the resultant spray granules with water at room temperature, using a glass pH electrode with liquid electrolyte filling in the form of a 3-molar KCl solution.

Example 2: Hygroscopicity Test on the Spray Granules

To determine the water absorption of the substance under test, it was exposed over a defined time period to defined standard conditions of 40° C. and 75% relative humidity. The water absorption was subsequently determined gravimetrically.

This was done using a climate chamber (e.g. VÖTSCH, VC0033), shallow weighing dishes with glass lid (diameter around 5 cm) and an analytical balance (readable to 0.0001 g).

For this procedure, 5 g of each homogeneous substance for determination were weighed out accurately and stored in the climate chamber for 1 h or 4 h under the defined standard climatic conditions in an open weighing dish. The weighing dishes, closed again after removal from the climate chamber, were each weighed and a determination was made of the weight increase (i.e. moisture absorption).

Here, the spray granulation product produced in accordance with the invention by means of a three-fluid nozzle according to Example 1 was compared with a spray granulation product produced beforehand by means of a two-fluid nozzle according to a process described in EP 16176371.9 (Example 5).

The moisture absorption of the spray granules produced with a two-fluid nozzle was 2% by weight after 1 h and 5.3% by weight after 4 h.

The moisture absorption of the spray granules produced with a three-fluid nozzle was 2% by weight after 1 h and 4.9% by weight after 4 h.

The hygroscopicity (water absorption) is lower for the spray granules produced with the three-fluid nozzle, and therefore more favourable than in the case of spray granules produced with the two-fluid nozzle.

Entirely analogously, comparative storage tests were conducted with the product from Example 1 and the product from Example 5 in EP 16176371.9 under defined standard conditions of 25° C. and 60% relative humidity over a period of 166 hours, and the water absorption was determined gravimetrically from time to time. The results are depicted in FIG. 5, and again show the lower water absorption of spray granules produced with a three-fluid nozzle by comparison with spray granules produced by a two-fluid nozzle.

Example 3: Caking Tendency Via Scratch Test

In the "scratch test" method using the texture analyser, a stainless steel rotor is immersed while rotating into a sample, which is abraded/"scratched off". The attendant forces act on the sensitive weighing system in the base plate. The greater the sticking together, the higher the force measured and hence the greater the caking tendency of the product.

For this purpose, use was made of a drying cabinet (e.g. MEMMERT, model UM 600), a climate chamber (e.g. VOTSCH, model VC 0033), metal cylinders with matching metal sleeve (cylinder: 0=50 mm, h=80 mm, m=1.3 kg, stainless steel), a Teflon disc as die underlay (80×80 mm, thickness 5 mm), a die weighting as application weight (metal cylinder, m=4 kg)

TA.XTPlus Texture Analyser (from STABLE MICRO SYSTEMS, sold by Winopal GmbH, Ahnsbeck) with software and accessories, a stainless steel rotor (diameter=40 mm), mounting facility for the metal sleeve and Teflon disc, a PC for data capture.

The measurements were conducted according to the following protocol:

Conditioning of sleeve, cylinder, weight and Teflon disc at 40° C. in the drying cabinet Sleeve is placed onto the Teflon disc 30 g of homogenized substance are introduced (determination is carried out 5 times in parallel) and the surface is levelled with a spatula in each case The cylinder is inserted into the sleeve and the whole assembly is placed into the climate chamber A 4 kg die weighting is placed onto the cylinder The weighted cylinders are then weathered by storage in the climate chamber for 24 hours at 40° C./75% relative humidity The die weighting is then removed Sleeve and cylinder are withdrawn together with the Teflon disc, and cooling takes place to room temperature for around 2 hours The cylinder is pulled out of the sleeve The sleeve remains on the Teflon plate, and is transferred to the mounting facility of the texture analyser and secured with the touch-and-close tape Using the software, the measuring procedure is started automatically as follows (parameters: penetration rate 2 mm/s; rotor velocity 10 rpm): When the rotor is lowered, the tray height is measured automatically and the depth of penetration is set at 75% of the tray height. The forces which arise as a result of the "scratching" are recorded and used for evaluating the force range from 20% to 60% (of the travel).

Evaluation:

To determine the caking tendency, the mean value of the force range for each measurement was used, reported for simplicity in [newtons/100]. The results of the multiple determination were again averaged.

The lower these values, the lower the caking tendency.

Here, the spray granulation product produced in accordance with the invention by means of a three-fluid nozzle according to Example 1 was again compared with a spray granulation product produced beforehand by means of a two-fluid nozzle according to a process described in EP 16176371.9 (Example 5).

The spray granules produced with the two-fluid nozzle showed a caking tendency of 228 newtons/100.

The spray granules produced with the three-fluid nozzle showed a caking tendency of 155 newtons/100.

The caking tendency for the spray granules produced with the three-fluid nozzle is much lower and hence more favourable than for the spray granules produced with the two-fluid nozzle. This product therefore has a greater tolerance to hot and moist conditions than conventional spray granules, and consequently has greater ease of handling.

DESCRIPTION OF THE FIGURES

Description for FIG. 1

1 Dust extractor (e.g. cyclone, filter, wet scrubber)
2 Pump (e.g. positive displacement pump)
3 Nozzle air (e.g. air, nitrogen)
4 Heating (e.g. electrical, steam, gas-fired)
5 Air supply fan
6 Sieve tray, Conidur plate
7 Fluidized bed, moving bed
8 Exhaust air fan 9 First aqueous solution or suspension (i)
10 Second aqueous solution or suspension (ii)
11 Gas volume flow rate measuring point, anemometer impeller
12 Temperature measuring point 1 (gas entry temperature)
13 Temperature measuring point 2 (fluidized bed temperature)
14 Temperature measuring point 3 (exhaust air temperature)

Description for FIG. 2

1 Nozzle air (e.g. air, nitrogen)
2 First aqueous solution or suspension (i)
3 Second aqueous solution or suspension (ii)
4 Air cap
5 Spray mist Description for FIG. 4

1: Comparison product from Example 5 of the EP application with application number 16176371.9 (1st measurement)
2: Comparison product from Example 5 of the EP application with application number 16176371.9 (2nd measurement)
3: Product produced using 3-fluid nozzle (1st measurement) Example 1
4: Product produced using 3-fluid nozzle (2nd measurement) Example 1

The invention claimed is:

1. A process for producing a particulate composition comprising methionine, methionylmethionine, potassium salt and ammonium sulfate by spray granulation, wherein:
 (a) a first aqueous solution or suspension (i), comprising 30 to 40% by weight ammonium sulfate,
  a second aqueous solution or suspension (ii), comprising 2 to 6% by weight methionine, 4 to 8% by weight methionylmethionine and 6 to 14% by weight potassium in the form of potassium salt and a gas,
 are sprayed via a three-fluid nozzle into a fluidized bed, with simultaneous evaporation of water in the fluidized bed, and with generation of crude particles, and optionally
 (b) the crude particles obtained in step (a) are dried.

2. The process according to claim 1, in which a second aqueous solution or suspension (ii), containing 3 to 5% by weight methionine and/or 5 to 7% by weight methionylmethionine and/or 8 to 12% by weight potassium in the form of potassium salt is used.

3. The process according to claim 1, in which the second aqueous solution or suspension (ii) is used in a weight ratio for the first aqueous solution or suspension (i) of 1.0/0.5 to 1.0/3.0.

4. The process according to claim 1, wherein air, nitrogen or $CO_2$ is used as gas.

5. The process according to claim 1, wherein step (a) of the process is carried out in a fluidized bed at a temperature in the fluidized bed of 60 to 130° C.

6. The process according to claim 1, further comprising the step of preparing the first aqueous solution or suspension (i), comprising ammonium sulfate, substantially by treating a gas mixture comprising hydrogen cyanide and ammonia, obtained in the production of hydrogen cyanide from methane and ammonia, with aqueous sulfuric acid and subsequently neutralizing the resulting aqueous solution with ammonia.

7. The process according to claim 1, further comprising the step of preparing the second aqueous solution or suspension (ii) by isolating a mother liquor formed in a process for producing methionine that comprises at least the steps of
 hydrolysing 5-(2-methylmercaptoethyl)hydantoin with potassium carbonate, potassium hydrogen carbonate to give aqueous potassium methioninate,
 neutralizing aqueous potassium methioninate with carbon dioxide to form methionine and subsequently crystallizing the methionine.

8. The process according to claim 1, in which the first aqueous solution or suspension (i) is additionally admixed with an amount of sulfuric acid such that after the spray granulation, a particulate composition is obtained which after dissolution in water has a pH of 3 to 6, measured on a 10% by weight aqueous solution of the particulate composition at room temperature with a glass pH electrode with liquid electrolyte filling in the form of a 3-molar KCl solution.

9. The process according to claim 1, in which, further, the aqueous solution or suspension (ii) used in step (a) is concentrated before step (a) by evaporation of water to give an aqueous suspension having up to 70% by weight solids content.

10. The process according to claim 1, in which an ammonium sulfate shell layer is applied to the particles obtained in step (b) by spraying with an aqueous solution containing 30 to 40% by weight ammonium sulfate with simultaneous evaporation of the water, the proportion of the ammonium sulfate shell layer formed on the particles being 5 to 30% by weight, based on the total weight of the particles formed.

11. The process according to claim 1, wherein the potassium salt is present as at least one salt of an inorganic or organic acid.

12. The process according to claim 11, wherein the potassium salt is at least one potassium salt selected from the group consisting of formic acid, acetic acid, propanoic acid, 2-hydroxypropanoic acid, 2-hydroxy-4-methylthiobutanoic acid, methionine, methionylmethionine, $KHCO_3$, $K_2CO_3$, $KHSO_4$ and $K_2SO_4$.

13. A fertilizer or fertilizer additive, comprising a composition produced by the process of claim 1.

* * * * *